US00PP14468P39

(12) United States Plant Patent
Pouw

(10) Patent No.: US PP14,468 P3
(45) Date of Patent: Jan. 20, 2004

(54) HYBRID TEA ROSE PLANT NAMED 'RUIRORAP'

(50) Latin Name: *Rosa L.*
Varietal Denomination: Ruirorap

(75) Inventor: Anton Pouw, De Kwakel (NL)

(73) Assignee: De Ruiter's Nieuwe Rozen B.V. (NL)

( * ) Notice: Subject to any disclaimer, the term of this patent is extended or adjusted under 35 U.S.C. 154(b) by 0 days.

(21) Appl. No.: 10/095,931

(22) Filed: Mar. 11, 2002

(65) Prior Publication Data

US 2003/0172417 P1 Sep. 11, 2003

(51) Int. Cl.[7] ..... A01H 5/00

(52) U.S. Cl. ..... Plt./140
(58) Field of Search ..... Plt./140

(56) References Cited

PUBLICATIONS

UPOV ROM GTITM Computer Database, GTI JOUVE Retrieval Software 2002/02, citation(s) for 'Ruirorap'.*

* cited by examiner

*Primary Examiner*—Bruce R. Campell
*Assistant Examiner*—W C Haas
(74) *Attorney, Agent, or Firm*—Christie, Parker & Hale, LLP

(57) ABSTRACT

A new and distinct Hybrid Tea Rose plant having attractive large Red flowers.

1 Drawing Sheet

Botanical desgnation: Rosa L.

BACKGROUND OF THE INVENTION

The present invention relates to a new and distinct variety of Rosa L. of the Hybrid Tea rose class, which was created by crossing as seed parent an unnamed, undistributed seedling and as a pollen parent the unpatented variety known as 'Tina'. The varietal denomination of this new rose is named 'Rutrorap.' The new variety was grown from a grafted cutting in The Netherlands.

SUMMARY OF THE INVENTION

Among the novel characteristics possessed by this new variety which distinguishes it from its parents and all other varieties of which I am aware are its bud shape and color.

Asexual reproduction by propagation of grafting of the new variety as performed in De Kwakel, The Netherlands shows that the foregoing and other distinguishing characteristics come true to form and are established and transmitted through succeeding propagation.

COMPARISON WITH PARENTS

Among other respects, the new variety differs from its parents in flower color, inasmuch as the seed parent has Pink flowers and the pollen parent has small Yellow flowers whereas the new variety has large Red flowers.

BRIEF DESCRIPTION OF ILLUSTRATION(S)

The accompanying illustration shows a typical specimen of 9-month old plants grown in a greenhouse in The Netherlands in the month of November of the new variety depicted in color as nearly true as is reasonably possible to make the same in a color illustration of this character.

DESCRIPTION OF THE NEW VARIETY

The following is a detailed description of the new variety with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

The following observations are made of 9-month old plants grown in a greenhouse in De Kwakel, The Netherlands during September from a grafted cutting.

FLOWER

Blooming habit: Continuous.

*Bud.*—Large length about 5 cm, width about 3.5 cm. Form: Cylindrical. Color: When sepals first divide, Red darker than 46A.

*Sepals.*—At top some leafy protrusion, 2 sepals also have some leafy protrusion on the margins, surface looks lovely. Size: Length about 4 cm, width at the base about 1 cm. Color: Upper Surface: Near 144A. Under surface: Near 144A and between 177A and 177B.

*Peduncle.*—Length: About 10 cm. Aspect: At the first 2 cm of the peduncle from the bottom are some small prickles about 1 mm in length; the surface of the upper part of the peduncle is smooth. Strength: Diameter about 4 mm. Color: Green Group, near 144A.

*Bracts.*—None observed.

Bloom:

*Size.*—Average size when fully opened — about 12 cm.

*Borne.*—Singly.

*Form.*—Upper part of flower is flat (shape-side view), Lower part is convex (shape-side view).

Petalage: Number of petals under normal conditions — about 22.

*Color* (⅓ *to* ½ *open*).—Outer Petals: Top surface — Red Group, darker than 46A, under surface — Red Group near 46A. Inner Petals: Top surface — Red Group darker than 46A, under surface — Red near 46A. General tonality from a distance: Red. Base of Petals (point of attachment): Very small White, near 155A.

Color (fully opened):

*Outer petals.*—Top surface — Red Group darker than 46A, under surface — Red Group near 46A.

*Inner petals.*—Top surface — Red Group darker than 46A, under surface — Red Group near 46A.

*General tonality from a distance.*—Red.

*Base of petals* (*point of attachment*).—Very small White near 155A.

*Color change.*—Color does not change as bloom ages.

*General tonality from a distance.*—Red.

Texture: Thick — wrinkled.

Appearance: Inside velvety; outside satiny.

Form: Nearly round, width about 6 cm, height about 6 cm.

Arrangement: Irregularly arranged.

Petaloids in center: About 5.

Persistence: Petals are persistent.

Fragrance: None.

Lasting quality:

*On the plant.*—About 20 days.

*In the vase.*—About 13 days, flower opens very slowly.

REPRODUCTIVE ORGANS

Stamens, filaments and anthers:

*Arrangement.*—Regularly arranged around styles.

*Color.*—Stamens Red Group near 53B, Filaments Red Group near 53B, Anthers Greyed-Yellow Group near 161B.

*Pollen.*—Color Greyed-White Group, near 156D.

*Styles.*—Bunched, uneven length.

*Stigmas.*—Color Grey-Yellow Group, near 161D.

*Hips.*—Shape: Pitcher shaped. Size: At full bloom, length about 1 cm at top, width about 1 cm at top. Color: The color of the hips, at full bloom, is near 144A.

PLANT

Form: Upright, long.

Growth: Uniform branching, very vigorous at moderate temperatures; height attained (first season) about 180 cm.

Foliage: Compound, 3, 5 to 7 leaflets.

*Size.*—Length about 15 cm, width about 11 cm.

*Quantity.*—About 11 leaves per stem, about 200 stems per $m^2$ per year.

*Color.*—New foliage: Upper side Purple Group near 187A; Under side Reddish Green Group, near 183A and 138B. Mature foliage: Upper side Green Group near 139A; Under side Green Group near 137C.

*Shape.*—Elliptic.

*Texture.*—Upper side: Smooth with deep-lying veins. Under side: Smooth with high-lying veins.

*Edge.*—Serrated.

*Serration.*—Serrate.

Petiole: Top surface Purple Group near 187A; Under surface near 138.

Stipules: Length about 2 cm, margin serrated, color middle: Light Green between 138B to 138D; margin, Dark Green near 139A.

Auricle: Absent.

Rachis: 1 to 3 prickles.

Resistance to disease: Susceptible to Blackspot, resistant to Mildew and Rust.

WOOD

New shoots:

*Bark.*—Smooth, Reddish Green Group near 177A and 146B.

*Wood.*—Light Green Group Near 146B.

Old wood:

*Bark.*—Smooth, Green Group near 1346.

*Wood.*—White Grey Group near 155C.

Flower stem: Between 70 to 100 cm from last cut (including peduncle).

Thorns:

*Quantity.*—Many small thorns (about 30 per stem) on basal canes at the basis, about 25 thorns per stem on laterals from basal canes.

*Form.*—Strong, curved downwardly, length about 1 cm, width about 0.5 cm, color (when young) Green near 146C, position irregular.

*Prickles.*—Some prickles at the basis of basal canes.

Winter hardiness: Not tested — glasshouse variety.

Uniqueness: Very good grow at moderate temperatures under glasshouse conditions, good bud shape and color.

I claim:

1. A new and distinct Hybrid Tea Rose plant of the variety substantially as shown and described.

* * * * *

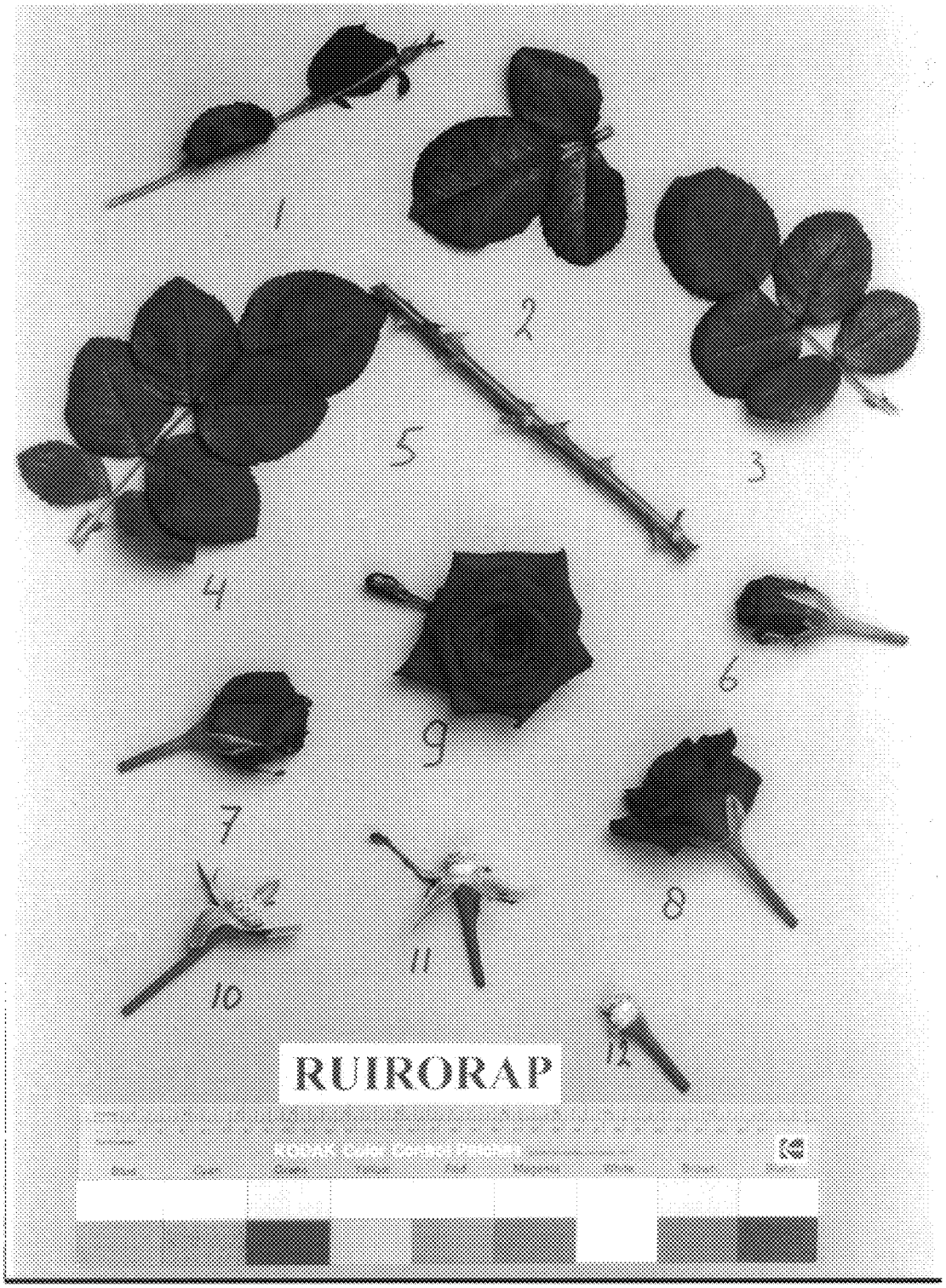
1
2
3
4
5
6
7
8
9
10
11
12
RUIRORAP